United States Patent [19]

Matay et al.

[11] Patent Number: 4,787,549

[45] Date of Patent: Nov. 29, 1988

[54] AUTOMATIC PIPE INSPECTION AND REPAIR SYSTEM

[75] Inventors: Istvan M. Matay, N. Royalton, Ohio; John D. Lydick, Manhattan Beach, Calif.

[73] Assignee: TRW, INC., Cleveland, Ohio

[21] Appl. No.: 575,370

[22] Filed: Jan. 30, 1984

[51] Int. Cl.$^4$ .............................................. B23K 15/00
[52] U.S. Cl. ........................................ 228/8; 228/102; 228/119; 209/518; 29/402.18; 427/34
[58] Field of Search ............... 228/103, 104, 102, 119, 228/8; 138/97; 427/142, 34, 46, 234, 239; 51/DIG. 33, 290; 29/402.18, 33 T; 73/49.5, 49.6, 49.1; 209/517, 518; 72/370; 901/42, 43

[56] References Cited

U.S. PATENT DOCUMENTS

| | | | |
|---|---|---|---|
| 2,979,196 | 4/1961 | Harmon | 209/518 |
| 3,263,809 | 8/1966 | Mandula | 209/518 |
| 3,711,310 | 1/1973 | Leeper | 427/34 |
| 3,805,945 | 4/1974 | Maeda | 209/517 |
| 3,815,738 | 6/1974 | Sweet | 209/518 |
| 4,067,490 | 1/1978 | Jones | 228/102 |
| 4,285,459 | 8/1981 | Baladjanian | 29/402.18 |
| 4,526,311 | 7/1985 | Schroder | 228/102 |

FOREIGN PATENT DOCUMENTS 3122044 12/1982 Fed. Rep. of Germany ........ 51/290

*Primary Examiner*—Kurt Rowan
*Attorney, Agent, or Firm*—Fay, Sharpe, Beall, Fagan, Minnich & McKee

[57] ABSTRACT

A tubing length or workpiece is conveyed to a readying apparatus (A) in which it is cleaned and otherwise readied for inspection. The readied tubing length is conveyed to an inspection and segregating apparatus (B). An ultrasonic array (20) inspects the tubing length, and as a result of the inspection, a switching system (26) places the inspected member on one of: an unrepairable workpiece conveyor (28); an acceptable workpiece conveyor (30); and, a repairable workpiece conveyor (32). The repairable tubing lengths are conveyed to a physical alteration apparatus (C). The physical alteration apparatus removes material, deposits material, hot isostatic pressure consolidates deposited material, and otherwise alters the repairable tubing lengths in such a manner as to bring them into conformity with preselected specifications. The altered tubing lengths are conveyed back to the inspection and segregating apparatus for reinspection. The acceptable tubing lengths are conveyed to a post-processing apparatus (D) which performs selected post-processing operations thereon, e.g., plastic coating. A computer implemented control (E) controls the inspection apparatus, the switching system, the physical alteration apparatus, and the post-processing apparatus such that tubing lengths are inspected and repaired quickly and efficiently.

7 Claims, 5 Drawing Sheets

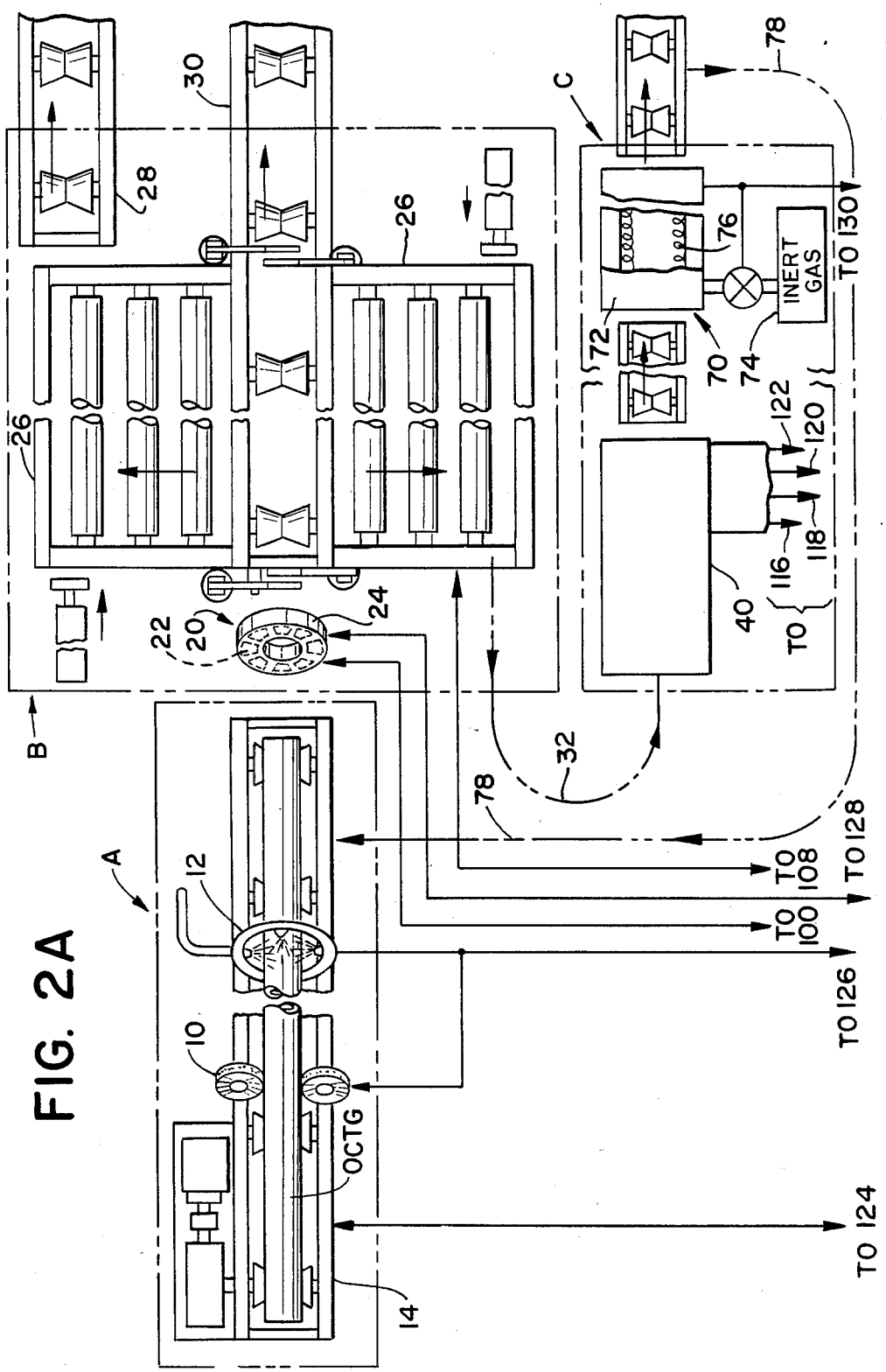

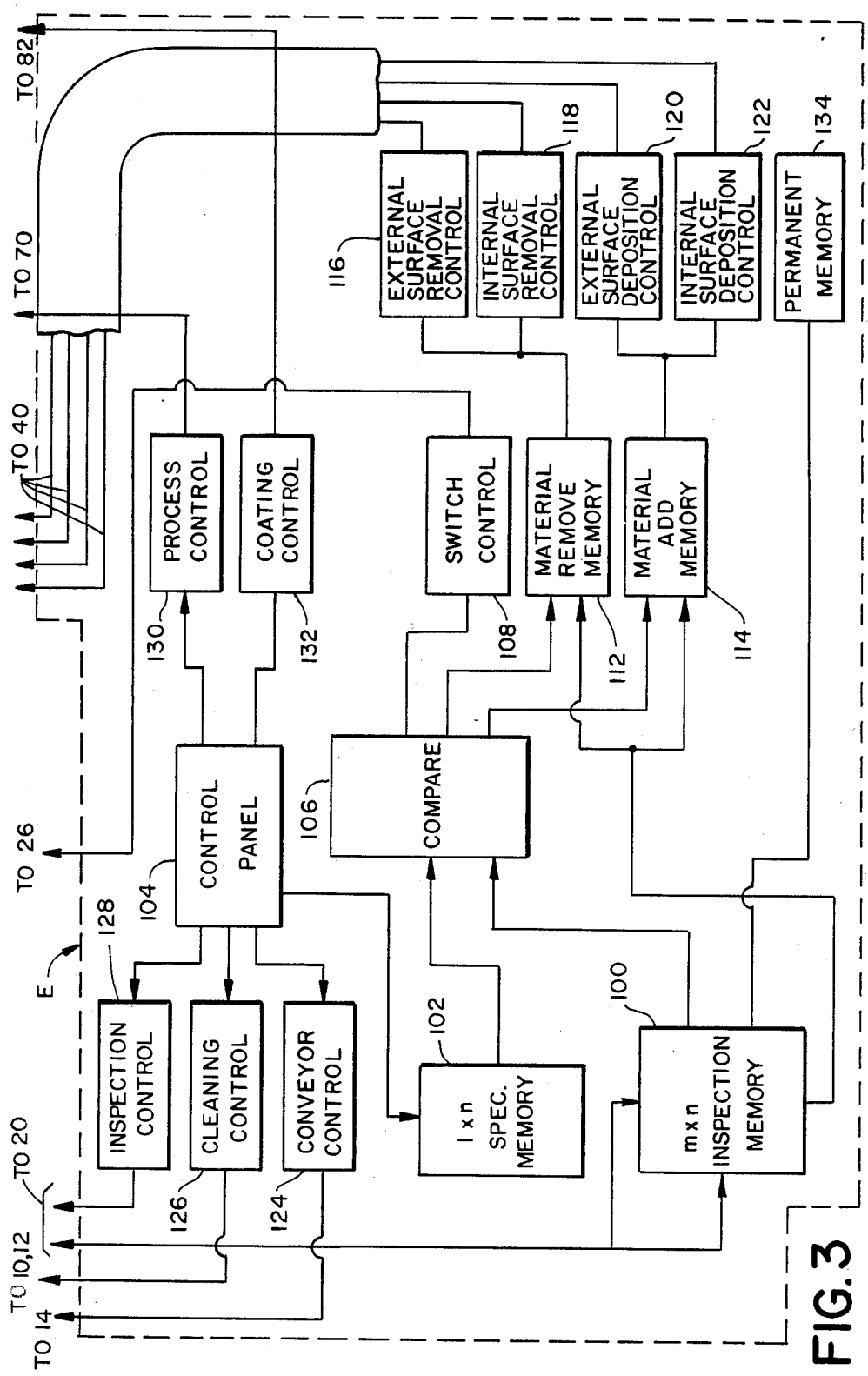

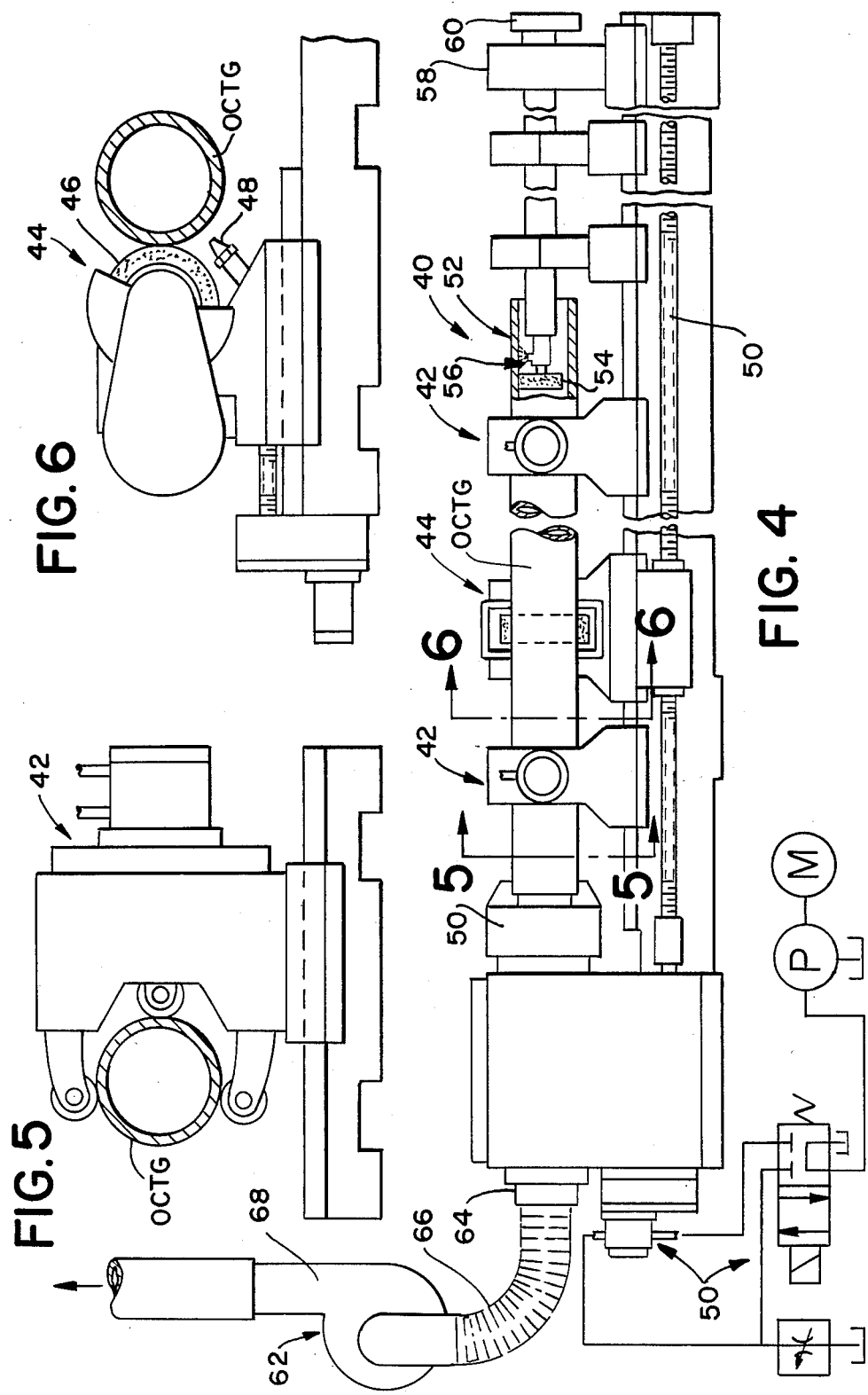

AUTOMATIC PIPE INSPECTION AND REPAIR SYSTEM

BACKGROUND OF THE INVENTION

The present invention relates to the art of quality maintenance. The invention finds particular application in the inspection and repair of tubular goods and will be described with particular reference thereto. It is to be appreciated, however, that the invention is also applicable to the inspection and processing of goods of various shapes and sizes including sheet goods, bars, spheres, irregular shaped parts, and the like.

Heretofore, tubular goods have been subject to tight quality control examination. Tubular goods such as oil well drilling pipe, nuclear reactor piping, and tubular goods used for other demanding applications have been inspected at the installation site. Commonly, a length of the tubular goods, e.g., a 50-foot length eight-inch steel pipe, was passed through an ultrasonic defect detection system. Defects in the tubular goods were noted and manually marked directly on the goods. Based on the inspection, the lengths were separated into acceptable, questionable, and rejected groups. The accepted lengths were installed in their normal, intended manner. When time permitted, surface cracks, such as stress risers, were manually removed. Due to their large length to diameter ratio, lengths with interior surface defects were usually scrapped.

One of the problems with the prior art inspection and repair systems was that an inventory of rejected goods was accumulated. At job sites where space is at a premium, e.g., off-shore drilling rigs and the like, maintenance of the inventory of rejected goods usurped valuable space. Another problem resided in the fact that the relatively high reject rate required a larger supply of uninspected goods to insure an adequate supply of acceptable goods. Further, the manual surface defect removal activities were time consuming and labor intensive. Frequently, a plurality of inspection and surface defect removal operations were required to locate, identify, and insure that all defects had been corrected.

The present invention contemplates a new and improved automated inspection as well as an automated repair system which overcomes the above-referenced problems and others while facilitating the ready availability of high quality tubular goods for installation.

SUMMARY OF THE INVENTION

In accordance with the present invention, a new method is provided for preparing tubular goods for installation. Lengths of tubing are readied for inspection by cleaning and the like. The readied tubing lengths are nondestructively inspected and compared with preselected specifications. Based on the inspection results, the tubing lengths are segregated at least into acceptable tubing lengths which conform with the preselected specifications and repairable tubing lengths which are physically alterable to be brought into conformity with the preselected specifications. The repairable tubing lengths are physically altered robotically in a manner which tends to bring them into conformity with the specifications.

In accordance with another aspect of the invention, apparatus is provided for preparing tubular goods. The apparatus includes readying means for readying lengths of tubing for inspection. A nondestructive inspection means inspects the readied tubing lengths, and a computer compares results of the nondestructive inspection with preselected specifications. Segregating means under control of the computer segregates the inspected tubing lengths at least into acceptable lengths which meet the preselected specifications and repairable lengths which are physically alterable to be brought into conformity with the preselected specifications. Physical altering means under control of the computer physically alters the repairable lengths in a manner which tends to bring them into conformity with the preselected specifications.

In accordance with more limited aspects of the invention, the step of and the means of physically altering the repairable tubing lengths accommodate removing metal from wall portions which are greater than a maximum thickness specification, depositing metal on wall portions which are less than a minimum thickness specification, removing and depositing metal to meet concentricity specifications, removing a defect and surrounding metal and depositing metal in replacement thereof, process treating the altered tubing lengths, coating the tubing lengths, and the like.

A primary advantage of the present invention is that it lowers the tubing rejection rate by automatically removing defects and building up thin wall regions as a part of an inspection process.

Another advantage of the invention resides in the quick and accurate repair and rebuilding of defective inspected goods.

Another advantage of the invention is that it enables the specifications at an installation site to conform to the immediate requirements of the intended use.

Yet another advantage of the present invention is found in the reduction of inventories of uninspected and rejected goods.

Still further advantages of the invention will become apparent to those of ordinary skill in the art upon a reading and understanding of the following detailed description of the preferred embodiment.

BRIEF DESCRIPTION OF THE DRAWINGS

The invention may take form in various steps and arrangements of steps or in various parts and arrangements of parts, a preferred embodiment of which will be described in this specification and illustrated in the accompanying drawing which form a part hereof and wherein:

FIGS. 2A and 2B illustrate apparatus for automatic pipe inspection and repair constructed in accordance with the present invention;

FIG. 3 illustrates a computer control system for controlling the apparatus of FIG. 2;

FIG. 4 is an elevational view in parallel cross-section of metal removal and depositing apparatus constructed in accordance with the present invention;

FIG. 5 is a cross-sectional view taken along lines 5—5 of FIG. 4; and,

FIG. 6 is a cross-sectional view taken along lines 6—6 of FIG. 4.

DETAILED DESCRIPTION OF THE PREFERRED EMBODIMENT

Figure 1:
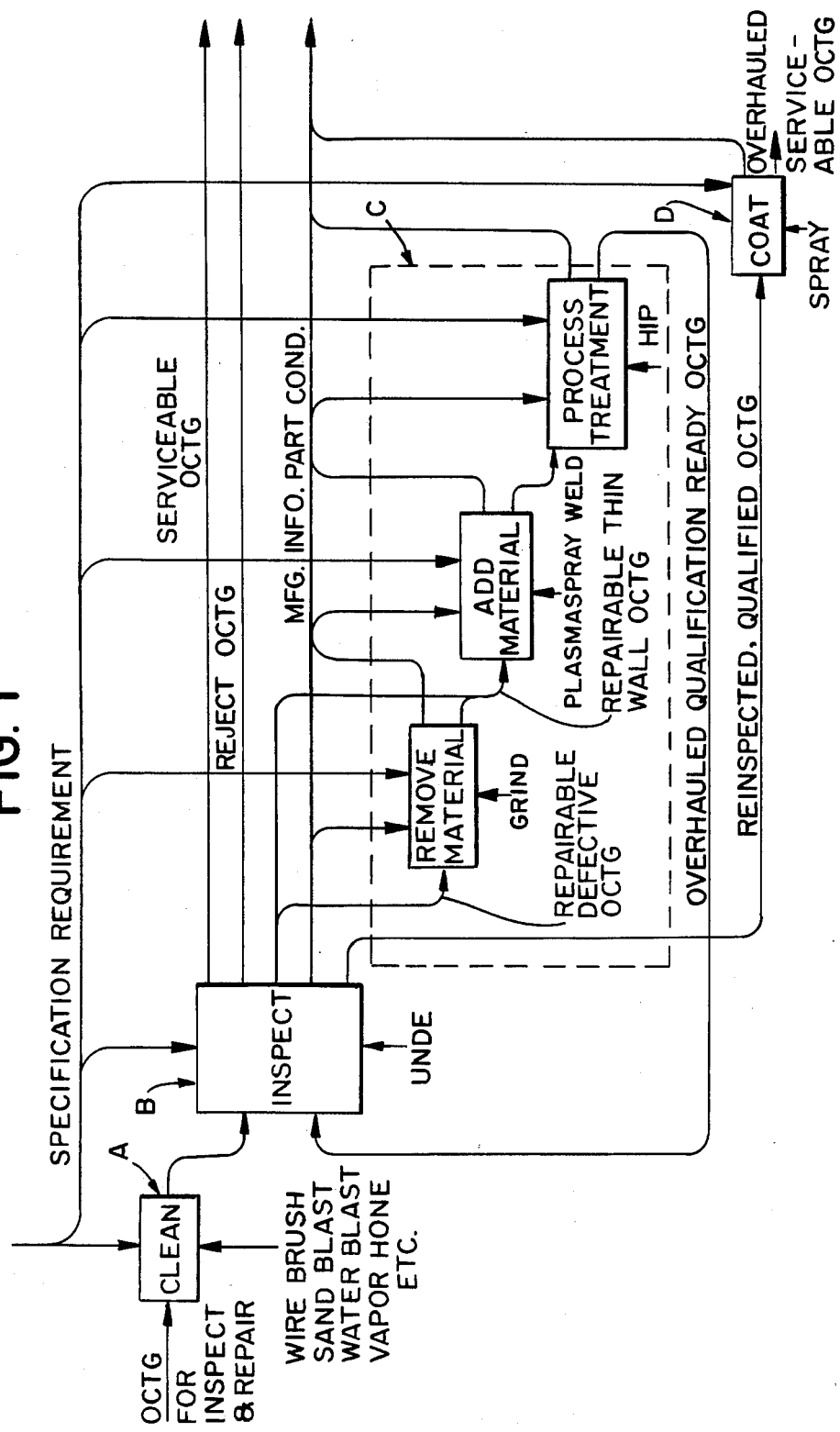
FIG. 1 is a block diagram illustrating a method of pipe inspection and repair in accordance with the present invention.
Figure 2B:
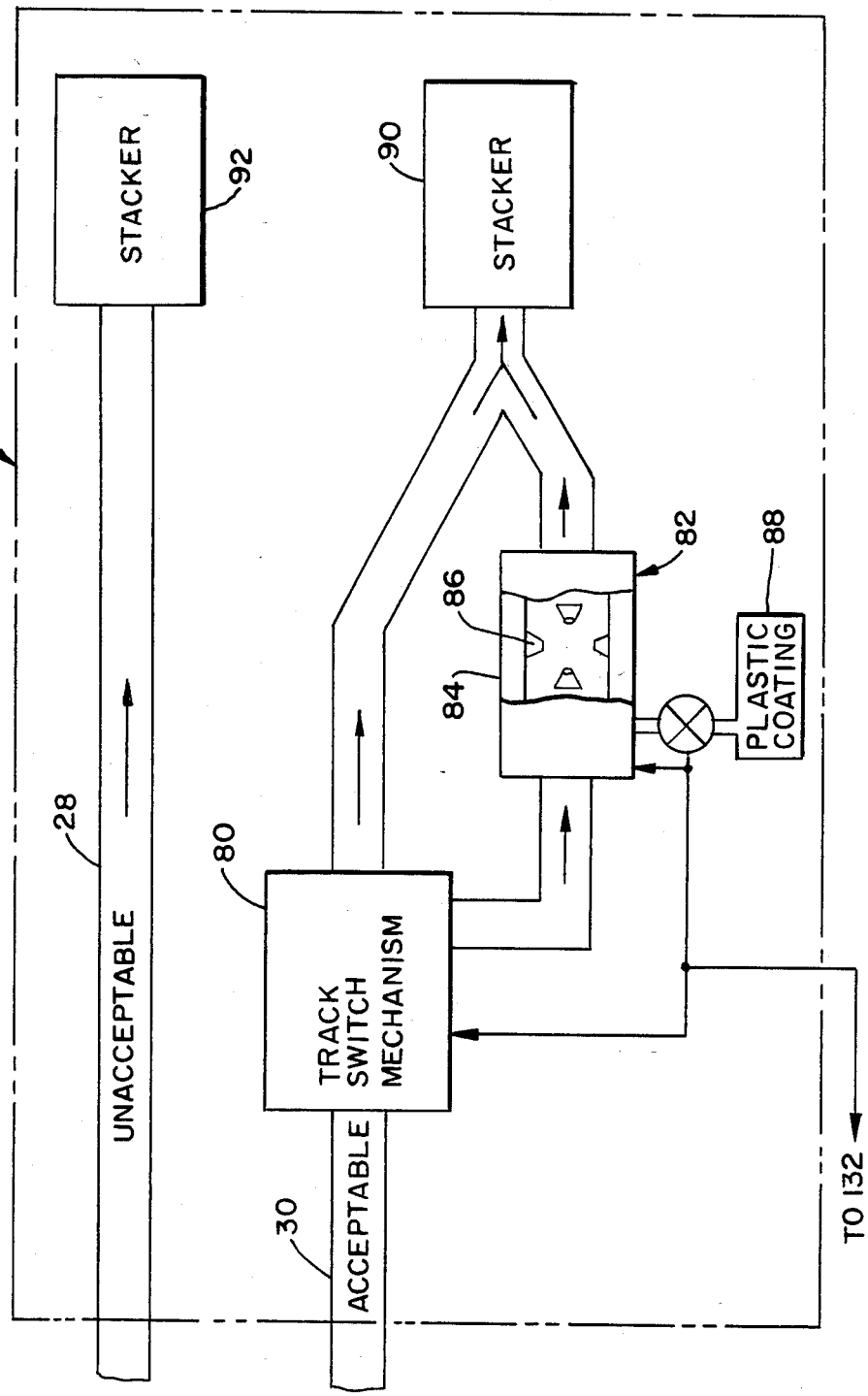

Referring now to the drawings wherein the showings are for purposes of illustrating a preferred embodiment of the invention only and not for purposes of limiting same, FIGS. 1, 2A, and 2B show a preliminary or readying step or means A to which each workpiece OCTG is subjected as it is readied for inspection. In the preferred embodiment described, it is to be appreciated that the workpieces OCTG comprise lengths of tublar goods. However, the invention is also applicable to use with other types of workpieces without in any way departing from the overall intent or scope of the invention. The readied workpiece then passes to a segregating step or means B segregation into one of a plurality of categories. In the preferred embodiment, three distinct categories are envisioned, namely: (1) acceptable or serviceable workpieces, (2) repairable workpieces, and (3) unrepairable or reject workpieces.

The workpiece in one or more of the segregated categories are next subjected to an automated physical alteration step or means C in which the physical characteristics are altered. In the preferred embodiment, such physical alteration includes the repair and/or reworking of out-of-specification workpiece characteristics. Subsequent to repair and/or reworking, the workpiece is again subjected to the inspection and segregating step or means B for determining into which segregation category the workpiece now falls. Optionally, a post-processing step or means D may perform processing operations on the acceptable workpieces, or workpieces of one or more of the other categories. A computer control system E (not shown in FIG. 1) preferably includes a supervisory central processor which supervises in a distributive fashion individual processors that control the reading step or means A, the segregating step or means B, the physical alteration step or means C, and the post-processing step or means D.

More particularly, and with reference to FIGS. 1 and 2A, the readying step or means A readies each workpiece OCTG for inspection. This readying includes workpiece cleaning, and in the arrangement of FIG. 2, wire brushes 10 and a series of waterjets 12 are utilized to clean the workpiece surface over the length thereof. Optionally, apparatus may be provided for sandblasting, vapor honing, or otherwise readying the workpiece to insure successful inspection.

A conveying means including a conveyor portion 14 conveys the readied workpiece to the segregating means B. The segregating step or means includes an ultrasonic inspection array 20 which ultrasonically, non-destructively examines (UNDE) the workpiece for defects, including wall thickness, concentricity, flaws, cracks, alloy type, and the like. Optionally, other non-destructive inspection techniques may be utilized, as appropriate. As is conventional and known in the art, the ultrasonic array includes a plurality of ultrasonic transducers 22 mounted within a fluid coupling containing housing 24. The transducers are disposed to transmit ultrasonic waves into the examined workpiece and to receive ultrasonic echoes from workpiece surfaces and defects.

A workpiece conveyor switching system 26 selectively switches the inspected workpiece onto one of three conveyor portions as determined by the results of the inspection. Specifically, the conveyor switching system switches workpieces which are shown by the inspection to be unrepairable onto an unrepairable or reject workpiece conveyor 28, switches workpieces which meet preselected specifications to a servicable or acceptable workpiece conveyor 30, and switches workpieces which are sufficiently close to the preselected specifications onto a repairable workpiece conveyor 32.

With particular reference to FIG. 1, the repairable, defective workpieces are repaired by a combination of steps including removing defective material, depositing or adding material on thin wall portions, and replacing removed defective material. In the preferred embodiment, the material adding step is performed with sufficient accuracy and uniformity that the built-up surface will meet the preselected specifications. Further, the physical properties of repaired regions of the workpiece may be improved with a material treating process such as hipping, i.e., hot isostatic pressure, heat treating, and the like.

Referring to FIGS. 2A, 4, 5, and 6, the repairable workpiece conveyor 32 conveys the tubing lengths to an apparatus 40 for depositing material thereon and for removing it therefrom. The material removal and deposition apparatus 40 includes a supporting structure 42 for supporting each workpiece OCTG during the metal removal and deposition operations. An exterior surface repair head 44 is mounted for movement relative to the workpiece to deposit and remove material from the exterior surface thereof. The exterior surface repair head includes exterior surface material removing means, such as a rotary grinder head 46, and exterior surface material depositing means, such as a plasma spray 48. Optionally, material may be deposited utilizing a deposition welder. An electro-hydraulic positioning means 50 positions the exterior surface repair head and the workpiece relative to each other such that the grinder is selectively positioned adjacent regions in which material is to be removed and the plasma spray is selectively positioned adjacent portions in which material is to be deposited or added.

An interior surface repair head 52 is disposed to move through the interior of the workpiece to remove and deposit material on the tubing interior surface. The interior surface repair head includes means for removing material, such as a rotary grinder head 54, and means for depositing material, such as a plasma spray 56. The interior surface repair head is movably mounted in supporting means 58 to undergo movement relative to the repairable workpiece under the control of the electro-hydraulic positioning means 50. A laser alignment system 60 maintains the path along which the interior surface repair head tracks in accurate, axial alignment with a central axis of the workpiece. This positions the interior surface repair head along the theoretical center line of the tubing. This enables the interior surface repair head to function as a radial dimension measurement means to establish tubing concentricity. An exhaust system 62 exhausts removed materials from the interior of the workpiece. A coupling 64 connects a flexible conduit 66 with one end of the workpiece, and an exhaust blower 68 draws loose material from the workpiece interior and discharges it to an appropriate waste collection system.

As best shown in FIG. 2A, a process treating means 70 improves the physical properties of the repaired areas of the workpiece. Although plasma spraying can achieve densities of better than 99.9%, it may still be desirable to enhance the properties of the deposited material. The treating means 70 includes a hot isostatic pressure unit comprising a selectively sealed chamber 72 for progressively receiving the sections of the workpiece therein. An inert hot gas supply means 74 selectively provides an isostatic atmosphere surrounding the workpiece interior and exterior surfaces. Induction heating coils 76 heat at least the repaired areas of the interior and exterior surfaces to provide elevated temperatures for the hot isostatic pressure treatment.

A return conveyor 78 conveys the repaired or overhauled qualification ready workpiece back to the inspection apparatus 20 to be reinspected. If the repair and overhaul have brought the workpiece into conformity with the specifications, the reinspection will result in the switching system 26 placing the workpiece on the acceptable or servicable conveyor 30. If the repairs have not brought the workpiece within the preselected specifications, the switching system will place the workpiece on the repairable workpiece conveyor 32 or the unrepairable or reject workpiece conveyor 28 as is appropriate from the results of the inspection.

With general reference to FIGS. 1 and 2A, and with particular reference to FIG. 2B, the post-processing step D in the preferred embodiment includes plastic coating the outer surface of the acceptable or reinspected, qualified workpieces or tubing lengths. If the workpiece have threaded ends, all or a selected portion of the threads may be retained free of plastic coating. A post-processing switching means 80 switches the acceptable workpieces from the acceptable workpiece conveyor to a conveyor which carries them to a plastic coating apparatus 82. This apparatus includes a housing 84 and a series of plastic coating spray heads 86 for spraying plastic material from a plastic material reservoir 88. Acceptable workpieces, whether plastic coated or uncoated, are conveyed to an acceptable workpiece stacking mechanism 90 which stacks the workpieces on pallets to store them until installation. Similarly, a second stacking means 92 is provided for stacking the unrepairable workpieces to readily facilitate their return to a scrap processing center.

FIG. 3 shows the computer control means E which controls the various apparatus components for cleaning, inspecting, segregating, reworking, and post-processing the workpieces. The computer control means includes an inspection memory 100 which stores data descriptive of the inspection of each workpiece. Specifically, in conjunction with each coordinate location, the inspection memory stores data indicative of workpiece physical properties, e.g., thickness of the side wall, workpiece concentricity, presence of a defect such as a crack, and the like.

A specification memory 102 is preprogrammed with preselected workpiece specifications entered at a central control panel 104. These workpiece specifications include the various physical characteristics which must be met or exceeded by workpieces which are classified as acceptable. A comparing means 106 compares the preselected specifications with the actual inspection data obtained at each coordinate location for an examined workpiece. If the comparing means 106 finds all the inspection data to be within the preselected specification requirements, a workpiece switching system control means 108 causes the conveyor switching system 26 to place the workpiece on the acceptable workpiece conveyor 30.

Similarly, should the workpiece not be acceptable, and depending upon whether it falls within or outside of predefined limits of the preselected specifications, the switching system control means 108 causes the switching system 26 to place the workpiece on one of the repairable and unrepairable workpiece conveyors, respectively. If the comparing means determines that the workpiece has too much material at any coordinate location, it causes a material removal memory 112 to store data indicative of the amount of material to be removed and the coordinate location at which such removal is required. In like manner, if the comparing means determines that material must be added to bring the workpiece within the preselected specifications, a material deposition memory 114 stores data indicative of the coordinate location and amount of material to be added.

An external surface material removal control means 116 and an internal surface material removal control means 118 retrieve the stored material removal data from the removal memory 112 for controlling the external and internal removal means 46 and 54 to thus remove the required amount of material. An external surface material deposition control means 120 and internal surface material deposition control means 122 retrive the stored material deposition data from deposition memory 114 for controlling the exterior and interior material deposition means 48 and 56 to deposit the required amount of material at each required location.

The central control panel 104 controls the conveying means for conveying the workpiece lengths through the system. Specifically, the central control panel causes a conveyor control means 124 to control the conveying of workpieces into the cleaning apparatus with preselected time intervals. A cleaning control means 126 causes the wire brushes, water jets, or other cleaning apparatus to clean each workpiece length as it is received. An inspection control means 128 controls the ultrasonic inspection array 20 causing it to inspect each received workpiece.

A treating process control means 130 controls the process treating apparatus 70. If the workpieces are to be plastic coated, a coating control 132 causes the post-processing switching means 80 to switch each acceptable workpiece to the plastic coating apparatus 82. Further, the coating control controls the coating apparatus. A permanent record means 134, such as a magnetic tape, computer printout, or the like, makes a permanent record of the inspection results of each workpiece for later reference.

The invention has been described with reference to the preferred embodiment. Obviously, modifications and alterations will occur to others upon a reading and understanding of this specification. It is intended to include all such modifications and alterations insofar as they come within the scope of the appended claims or the equivalents thereof.

Having thus described the invention, it is now claimed:

1. An apparatus for preparing tubular workpieces having interior and exterior surfaces, said apparatus comprising:
   a readying means for readying said workpieces for inspection;
   an inspecting means for nondestructively inspecting the workpiece to measure wall thickness and concentricity between the interior and exterior surfaces along the workpiece;
   a comparing means for comparing the measured wall thickness and concentricity with preselected wall thickness and concentricity specifications;
   a switching means for separating the inspected workpieces at least into acceptable workpieces which conform with the preselected specifications and repairable workpieces which are physically alterable to conform with the preselected specifications;

an interior surface repair head disposed to be positioned longitudinally within the workpiece, the interior surface repair head including an interior surface material depositing means for selectively depositing material on interior surfaces of the workpiece and an interior surface material removing means for selectively removing material from interior surfaces of the workpiece;

an exterior surface repair head disposed to be positioned longitudinally along exterior surfaces of the workpiece, the exterior surface repair head including an exterior surface material depositing means for selectively depositing material on exterior surfaces of the workpiece and an exterior surface material removing means for selectively removing material from the exterior surfaces; and, repair head control means for selectively positioning the interior and exterior surface repair heads along the workpiece and for controlling the interior and exterior surface material depositing and removing means.

2. The apparatus as set forth in claim 1 further including conveying means for conveying the workpieces from the readying means to the inspecting means.

3. The apparatus as set forth in claim 2 further including coating means for coating acceptable workpieces, the conveying means further conveying acceptable workpieces from the inspecting means to the coating means.

4. The apparatus as set forth in claim 1 further including process treating means for treating the portions of repairable workpieces on which material has been deposited.

5. The apparatus as set forth in claim 1 wherein the exterior and interior surface material removing means each include a rotary grinder.

6. The apparatus as set forth in claim 1 wherein the exterior and interior surface material depositing means each include plasma spray deposition means.

7. The apparatus as set forth in claim 1 wherein the exterior and interior surface material depositing means each include welding deposition means.

* * * * *

UNITED STATES PATENT AND TRADEMARK OFFICE
CERTIFICATE OF CORRECTION

PATENT NO. : 4,787,549
DATED : November 29, 1988
INVENTOR(S) : Matay, et al

It is certified that error appears in the above-identified patent and that said Letters Patent is hereby corrected as shown below:

Column 3, line 32, "control the reading step" should read -- control the readying step --.

Signed and Sealed this

Twentieth Day of June, 1989

Attest:

DONALD J. QUIGG

*Attesting Officer*  *Commissioner of Patents and Trademarks*